United States Patent [19]
Walaszek et al.

[11] Patent Number: 5,561,160
[45] Date of Patent: Oct. 1, 1996

[54] FORMULA AND METHOD FOR THE PREVENTION AND TREATMENT OF HYPERCHOLESTEROLEMIA AND CELLULAR HYPERPROLIFERATIVE DISORDERS

[76] Inventors: Zbigniew Walaszek, 1324 Makaha Dr., Bastrop, Tex. 78602; Thomas J. Slaga, 2006 Plembrook Dr., Austin, Tex. 78734; Margaret Hanauek, 1324 Makaha Dr., Bastrop, Tex. 78602

[21] Appl. No.: 317,790

[22] Filed: Oct. 4, 1994

Related U.S. Application Data

[62] Division of Ser. No. 12,145, Jan. 28, 1993, Pat. No. 5,364,644, which is a continuation of Ser. No. 525,384, May 16, 1990, abandoned.

[51] Int. Cl.$^6$ .................................................. A61K 31/19
[52] U.S. Cl. .................................................. 514/574
[58] Field of Search .................................................. 514/574

[56] References Cited

U.S. PATENT DOCUMENTS

| | | | |
|---|---|---|---|
| 3,697,287 | 10/1972 | Winitz | 99/1 |
| 4,751,085 | 6/1988 | Gaull | 514/474 |
| 4,845,123 | 7/1989 | Walaszek et al. | 514/473 |
| 5,364,644 | 11/1994 | Walaszek et al. | 514/574 |

FOREIGN PATENT DOCUMENTS

| | | |
|---|---|---|
| 2651947 | 5/1978 | Germany. |
| 7712421 | 11/1977 | Netherlands. |

OTHER PUBLICATIONS

Berkon et al., "The Merck Manual", published 1982 by Merck Sharp & Dohme Research Labs (N.J.) see pp. 970–977.

Garrison et al. "The Nutrition Desk Reference" published 1985 by Keats Publishing Inc., (Conn) see pp. 172–180.

*Primary Examiner*—Raymond Henley, III
*Attorney, Agent, or Firm*—David G. Henry

[57] ABSTRACT

The present invention provides a formula and method for the prevention and treatment of hypercholesterolemia and cellular hyperproliferation. More specifically, the present invention provides a method for administering a formula including glucaric acid or a pharmaceutically acceptable salt thereof for the prevention and treatment of hypercholesterolemia and cellular hyperproliferation in humans and animals. It has been determined that glucaric acid and pharmaceutically acceptable salts thereof significantly lower the total and LDL level of serum cholesterol and inhibit cellular hyperproliferation when administered in therapeutic amounts. It is intended that glucaric acid or a pharmaceutically acceptable salt thereof is employed alone or in combination with other medicinal agents for the prevention and treatment of hypercholesterolemia and cellular hyperproliferation.

24 Claims, No Drawings

FORMULA AND METHOD FOR THE PREVENTION AND TREATMENT OF HYPERCHOLESTEROLEMIA AND CELLULAR HYPERPROLIFERATIVE DISORDERS

This is a divisional application of application Ser. No. 08/012,145 filed Jan. 28, 1993, now U.S. Pat. No. 5,364,644 which is a continuing application of Ser. No. 07/525,384 filed May 16, 1990 now abandoned.

BACKGROUND OF THE INVENTION

Hypercholesterolemia and cellular hyperproliferative disorders are causative factors in several different pathologies, many of which cause death. For example, hypercholesterolemia, also including hyperlipidemia for purposes of the present invention, is a contributing factor in the development of heart disease and stroke. Heart disease is the single biggest cause of death in the United States. Cellular hyperproliferative disorders include such diseases as psoriasis vulgaris, dysplastic skin diseases, pigmentary skin diseases, Kaposi's sarcoma; chronic adult respiratory syndrome, large granular lymphocyte/natural killer cell proliferative disease, haemopoietic proliferative disorders, B-cell proliferative disorders, pigmented villonodular synovitis, proliferative diseases of retinal cells, and some cancers. Although several of the cellular proliferative disorders only cause discomfort and patient suffering, several, such as cancer, may be fatal. In the United States alone, tens of thousands of people die from cancer each year, and additional tens of thousands suffer from the numerous other cellular hyperproliferative disorders.

High levels of blood cholesterol and blood lipids are conditions involved in the onset of arteriosclerosis. Arteriosclerosis is a major factor in the development of heart disease and stroke. Among the numerous studies into the origin of hyperlipidemia, and familiar hypercholesterolemia, various dietary components, such as, lipids, proteins, carbohydrates, dietary fibers, and trace metals, have been investigated. It is commonly assumed that plethoric diets high in fats and cholesterol are a major cause in the development of hypercholesterolemia. Moreover, plethoric diets are known to be associated with increased levels of low density lipoproteins (LDL), very low density lipoproteins (VLDL), and high density lipoproteins (HDL) (1,2).

Studies have shown that the incidence of coronary heart disease rises in linear fashion with the level of serum cholesterol. In the United States coronary heart disease kills many thousands of people annually. Because high serum cholesterol levels are directly related to coronary heart disease, reducing serum cholesterol levels is a major health concern in the United States.

Serum cholesterol levels that are generally accepted as within normal ranges in the United States are higher than those found among comparable individuals in populations with a low incidence of arteriosclerosis. The optimal serum cholesterol for a middle-aged American man is probably about 200 mg/100 ml, or less. For practical purposes, hypercholesterolemia is generally defined as any value above the 95th percentile for the population, which in Americans ranges from about 230 mg/100 ml in individuals less than 20 years old, to about 300 mg/100 ml in individuals greater than 60 years old. These limits are, however, probably excessive because of the known risk of cholesterol values at these levels. As an alternative method, practicing physicians frequently use a convenient rule of thumb which holds that any level of serum cholesterol greater than about 200 mg/100 ml plus the person's age should be considered abnormal. Even these limits may be too high.

Once a patient has been diagnosed as suffering from hypercholesterolemia the first, and most common, method of therapy is diet modification, e.g.., the strict avoidance of the sources of cholesterol and saturated fats. The patient is instructed to avoid meat, especially organ meats and obviously fat, egg, whole milk, cream, butter, lard, and saturated cooking fats. These foods are replaced in the patient's diet with foods low in saturated fat and cholesterol, e.g., fish, vegetables, poultry, polyunsaturated oils, and margarine. However, because this therapy requires a dramatic lifestyle change and the substituted foods are generally less flavorful, patient compliance is very poor.

Once it is determined that dietary restrictions have not accomplished the desired end, pharmaceutical therapy is instituted. Hypocholesterolemic agents enjoy wide use and acceptance in the medical community as an alternative to dietary restrictions. Cholestyramine, a bile acid sequestrant, is a hypocholesterolemic agent which is effective in lowering serum cholesterol, especially when coupled with diet restrictions. A dosage of about 16 to about 32 grams in 2 to 4 divided daily doses will, for example, lower LDL levels by 25 to 50%, probably by increasing LDL removal. However, cholestyramine is associated with side effects, such as constipation and poor taste that limit general patient acceptance. Further, cholestyramine and another hypocholesterolemic drug, candicidin, apparently increased azoxymethanol-induced bowel tumorigenesis in the rat (3,4).

A further hypocholesterolemic agent, niacin is useful in hypercholesterolemia, but the high dosage required, three to nine grams per day in divided dosage with meals, coupled with the side effects of gastric irritability, hyperuricemia, hyperglycemia, flushing and pruritus, prevents its general use. Niacin is most effective when combined with cholestyramine.

Thyroid analogs, e.g., D-thyroxine, effectively lower LDL levels, but are contraindicated in patients with suspected or proven heart disease. Further, since these agents mimic thyroid hormone, they produce a plethora of untoward effects in the body. Accordingly, these agents have no little or no place in the therapy of the typical hypercholesterolemia patient. Other agents which are presently utilized are generally less effective than strict dietary management.

Heart disease kills tens of thousands of Americans every year. The major cause of heart disease is the accumulation of plaque in the coronary arteries. This accumulation is presumably cause by excessively high levels of serum cholesterol. However, there is still no effective hypocholesterolemic agent commercially available that has found wide patient acceptance.

In light of the enormity of this problem, it would be extremely advantageous to provide a hypocholesterolemic agent which effectively lowers serum cholesterol in a human without the attending side effects typically associated with previous hypocholesterolemic agents. Further, it would be advantageous to provide a hypocholesterolemic agent which is effective when administered to a patient in need thereof in a relatively small dose. Another and important advantage is realized by providing a hypocholesterolemic agent which is administered multiple times or once daily, particularly if a slow release formulation is used. It would also be advantageous to provide a hypocholesterolemic agent which is incorporated into a vehicle, such as a multivitamin and mineral tablet, and administered daily to the general population to prophylactically protect the population against hypercholesterolemia. A still further advantage would be realized in providing a hypocholesterolemic agent which is safely, and inexpensively added to foodstuffs intended for consumption by the general population, and thereby provide prophylactic protection against hypercholesterolemia.

Cellular hyperproliferative disorders are generally characterized by the hyperproliferation and incomplete differentiation of cells. For example, in psoriasis vulgaris there is a hyperproliferation of incompletely differentiated cells of the epidermis. Presently, it is not fully understood what causes certain cells to reproduce rapidly when the host has no apparent need for them. Since growing evidence suggests that cellular hyperproliferation is involved with chemically induced carcinogenesis, the inhibition of cellular proliferation may also be an effective tool for prevention of certain cancers. Accordingly, the inhibition of cellular proliferation may be an effective tool for preventing psoriasis vulgaris, dysplastic skin diseases, pigmentary skin diseases, Kaposi's sarcoma and several other diseases associated with the hyperproliferation of cells such as chronic adult respiratory syndrome, large granular lymphocyte/natural killer cell proliferative disease, haemopoietic proliferative disorders, B-cell proliferative disorders, pigmented villonodular synovitis, or hairy cell leukemia, or proliferative diseases of retinal cells, for example. In light of the relation between the hyperproliferation of cells and several diseases, it would be extremely advantageous to provide an antiproliferation agent which effectively inhibits cellular hyperproliferation in a human with little or no side effects. Further, it would be beneficial to have an antiproliferative agent which is effective when administered to a patient in need thereof in a relatively small dose. Another and important advantage is realized by providing an antiproliferative agent which may be administered once daily. It would also be advantageous to provide an antiproliferative agent which is incorporated into a vehicle, such as a multivitamin and mineral tablet, and administered daily to the general population to prophylactically protect the population against cellular hyperproliferation. A still further advantage would be realized in providing an antiproliferative agent which is safely, and inexpensively added to foodstuffs intended for consumption by the general population, and thereby provide prophylactic protection against the disease typically associated the with hyperproliferation of cells.

Considering the morbidity and mortality created by both of the above condition, i.e., hypercholesterolemia, and the hyperproliferation of cells, it would be extremely advantageous to provide one agent which prevented or treated both conditions simultaneously. Further, since both conditions affect the general population, it would be advantageous to provide a sustained release preparation, such as a multivitamin and mineral tablet which could be administered to prevent these conditions in the general populations. It would also be of benefit to provide a multivitamin and mineral preparation which contained agents which acted synergistically to prevent or treat hypercholesterolemia and the hyperproliferation of cells.

SUMMARY OF THE INVENTION

One aspect of the invention is directed to a method for the prevention and treatment of hypercholesterolemia. A further aspect of the present invention is directed to a method for the prevention and treatment of cellular hyperproliferation. According to this method, an animal is administered a pharmaceutical formulation including a therapeutically effective amount of glucaric acid or a pharmaceutically acceptable salt thereof. The animal is preferably a human. The pharmaceutical formulation may be a tablet, capsule, suspension, or solution. The pharmaceutical formulation may be administered by mouth or by injection. The pharmaceutically acceptable salt is preferably selected from the groups consisting of calcium glucarate, sodium glucarate, potassium hydrogen glucarate, and magnesium glucarate.

In accordance with a preferred embodiment, a human is administered daily a sustained release pharmaceutical formulation including from about 200 mg to about 8,000 mg of glucaric acid or a pharmaceutical acceptable salt thereof. In combination with the glucaric acid the pharmaceutical formulation also includes a multiplicity of vitamins, minerals and micronutrients. The preparation is intended as prophylactic protection against the onset of hypercholesterolemia and cellular hyperproliferation.

As an alternative to the above preferred embodiment, a method is provided for the prevention of hypercholesterolemia and/or cellular hyperproliferation in a population of humans and animals. The method provides for adding to a selected foodstuff a predetermined amount of glucaric acid or a pharmaceutical acceptable salt thereof, and thereafter, providing a sufficient quantity of the foodstuff to the population of humans and animals such that the humans and animals ingest a therapeutically effective amount of glucaric acid or a pharmaceutically acceptable salt thereof.

DESCRIPTION OF PREFERRED EMBODIMENTS

The present invention provides a formula and method for the treatment of hypercholesterolemia and cellular hyperproliferation. More specifically, the present invention provides a method for administering a formula including glucaric acid or a pharmaceutically acceptable salt thereof for the prevention and treatment of hypercholesterolemia and cellular hyperproliferation in humans and animals. It has been determined that glucaric acid, and the pharmaceutically acceptable salts thereof, significantly lower the total level of serum cholesterol and LDL in animals when administered in therapeutic amounts while simultaneously inhibiting cellular hyperproliferation. It is intended that glucaric acid or a pharmaceutically acceptable salt thereof is employed alone or in combination with other medicinal agents for the prevention and treatment of hypercholesterolemia and/or cellular hyperproliferation.

D-Glucaric acid (glucaric acid) is a six-carbon, straight-chain dicarboxylic acid and is sometimes referred to as D-saccharic acid. Chemically, a schematic formula for D-glucaric acid is COOH—(CHOH)$_4$—COOH. The salts of D-glucaric acid (glucaric acid) are referred to as D-glucarates (glucarates), e.g., calcium glucarate, sodium glucarate, magnesium glucarate, and potassium hydrogen glucarate.

Glucaric acid and the salts thereof are normal metabolic products in mammals. In both human and rat liver (5) as well as skin (6) glucuronic acid was found to be enzymatically oxidized to glucaric acid. Glucaric acid is the sole end product of the glucuronic acid pathway in guinea pigs and primates (7). Significant interindividual differences have been reported (8) in normal healthy populations. It was observed (9) that the urinary excretion of glucaric acid in cancer patients and tumor-bearing rats was significantly lower than in healthy controls. In mice with experimental tumors and in cancer patients, uninvolved liver tissue was found to have a lowered glucaric acid level (7). Further, studies have shown that cancerous tissues lack the glucaric acid-synthesizing system (7).

The physiological function of glucaric acid/glucarate remains unclear, although it appears to be an important carbohydrate for cell viability and homeostasis. It is not known if glucaric acid is an essential nutrient for normal subjects. Some plants have been analyzed as identifiable sources rich in glucaric acid (10,11). Recently glucaric acid/glucarate have been found in cruciferous vegetables (12). Glucaric acid/glucarate content is high in young seedlings and sprouts but low in respective seeds (13). Glucaric acid/glucarates are generally non-toxic, and no adverse effects have been observed from prolonged feeding of potassium hydrogen glucarate to rats (14,15) or calcium glucarate to rats (16) and mice (17).

In accordance with one important aspect of the present invention, a medicament is provided including therapeutic amounts of glucaric acid or a pharmaceutically acceptable salt thereof useful in the treatment and prevention of hypercholesterolemia cellular and hyperproliferation. With respect to hyperproliferation, the present inventors have determined that, by administering therapeutic amounts of glucaric acid/glucarate, total serum cholesterol could be significantly reduced. Studies with this compound demonstrated that HDL, LDL, and VLDL were reduced and, most significantly, serum LDL was reduced. Further, studies have shown that glucarates are generally non-toxic and cause little or no side effects in the individual being treated.

With respect to the antiproliferative effects of glucaric acid, the present inventors have determined that glucaric acid inhibits cellular hyperproliferation in animals. Since cellular hyperproliferation is related not only to the development of certain cancers but also other diseases, e.g., psoriasis vulgaris, dysplastic skin diseases, pigmentary skin diseases, Kaposi's sarcoma and several proliferative disorders, it is believed that the use of glucarates for this purpose would be a significant departure from prior method of preventing or treating diseases associated with cellular hyperproliferation.

In accordance with one aspect of the present invention, a method is provided wherein an individual in need thereof is administered a pharmaceutical formulation including a therapeutically effective amount of glucaric acid or a pharmaceutically acceptable salt thereof. The inventive method is intended to reduce cholesterol in those individuals suffering from hypercholesterolemia and to inhibit cellular hyperproliferation in those individuals in need thereof. Further the formulation and method is intended to prevent the onset of hypercholesterolemia and/or cellular hyperproliferation in those individuals at risk of developing it. The present inventors have demonstrated that glucarates significantly lower total serum cholesterol in rats, and it is believed that this therapeutic effect will also be observed in humans. Moveover, the present inventors have also demonstrated that glucarates inhibit cellular proliferation. It is intended that this discovery be applied beneficially to treat those individuals suffering from cellular hyperproliferation disorders.

Glucaric acid or glucarates may be compounded in numerous acceptable pharmaceutical formulations. Preferable pharmaceutical formulations include tablets, capsules, insuflations, syrups, suspensions, solutions, suppositories, injections, and any sustained release preparation thereof. More preferable, the compound is incorporated into a sustained release tablet or capsule which will provide a hypocholesterolemic and antiproliferative therapeutic effect for the longest possible duration. Thus, the individual receives the maximum benefit from the compound, and patient compliance is increased because the dosage form is administered daily. Injections which are useful in the practice of the present invention include intravascular (e.g., intravenous or intraarterial) subcutaneous, intramuscular, intralymphatic, intraperitoneal, and intrapleural. The most preferable route of the administration for an injection is, however, intravenous.

The pharmaceutical formulation administered to the individual in need thereof preferably includes a therapeutically effective amount of glucaric acid or a pharmaceutically acceptable salt thereof. Preferably the individual is administered daily from about 10 mg to about 16,000 mg of glucaric acid or a pharmaceutically acceptable salt thereof per day compounded as a single or divided dose. More preferably the individual is administered from about 200 mg to about 8,000 mg per day.

The preferred pharmaceutically acceptable salt of glucaric acid includes any salt of glucaric acid which is both non-toxic and does not substantially diminish the therapeutic effect of the compound. For example, preferred pharmaceutically acceptable salts of glucaric acid include calcium glucarate, sodium glucarate, magnesium glucarate, and potassium hydrogen glucarate. More preferably, however, the pharmaceutical formulation includes potassium hydrogen glucarate and/or calcium glucarate.

In accordance with a further aspect of the invention, glucaric acid and/or glucarate is incorporated as a hypocholesterolemic or antiproliferative agent into nutritional compositions containing vitamins, minerals and/or other micronutrients, e.g., a multivitamin and mineral preparation. Preferably, the glucarate moiety acts as a carrier for minerals such as calcium and potassium. According to this embodiment of the invention, glucarates are included in therapeutic, non-toxic, amounts in a multivitamin supplement as a preventive measure to protect the general population against the onset of hypercholesterolemia and/or cellular hyperproliferation. Such formulas may be prepared according to manufacturing techniques well know in the pharmaceutical art, and in a variety of dosage forms, such as, tablets, capsules, and liquids or sustained release formulations thereof.

According to a further aspect of the invention, glucaric acid and/or glucarates are incorporated in therapeutic amounts into foodstuffs and are consumed by the general population. Presently, many foodstuffs are enriched by the addition of vitamins and mineral supplements, for example, breads, cereals, milk and fruit juices. Glucarates may be added to these products in the same conventional manner in which vitamins or minerals are added to enrich foods. For example, calcium glucarate or potassium hydrogen glucarate may be added to a food product, thereby advantageously providing both a mineral supplement, e.g., calcium and potassium, and prophylactic protection against the onset of hyperproliferative diseases and hypercholesterolemia. Accordingly, the further enrichment of these products with glucaric acid and/or a glucarate will advantageously provide the consuming public with an inexpensive, safe, and convenient alternative for preventing the onset of hyperproliferative diseases and hypercholesterolemia.

As indicated herein above, glucarates are safe, effective hypocholesterolemic and antiproliferation agents. In accordance with one aspect of this invention, glucarate is preferably utilized or administered in combination with a multivitamin and mineral formulation. Preferably, such a formulation is administered as a single sustained release dose.

The following examples are presented to illustrate preferred embodiments of aspects of the present invention but are not intended to limit the scope of the invention unless otherwise specifically so stated in the claims appended hereto.

EXAMPLE 1

Hypocholesterolemic and Antiproliferative Properties of Glucarate-Containing Nutritional Compositions Calcium D-glucarate was incorporated to the AIN-76A diet (18,19) at the concentration of 17.5 or 35 mmol/kg diet with no changes in the level of any essential micronutrient. Specifically there was no change in the level of calcium and phosphorus. The AIN-76A or glucarate-containing AkN-76A diets were fed ad libitum to female Sprague-Dawley rats beginning at 40 days of age. Food intake and body weight were monitored periodically. There was no statistically significant difference in food intake or weight gain. DNA labeling indices were measured in 55-day-old rats. Four animals from each dietary group were injected at 9:00 a.m. with a single intraperitoneal dose of [$^3$H-methyl]thymidine (1.0 μCi/g body weight; specific activity 88 Ci/mmol (Amersham, Arlington Heights, Ill.) Animals were fasted overnight before they were injected with [$^3$H-methyl]thymidine. The animals were sacrificed one hour after injection. Colons and small intestines were removed and processed for histology, followed by autoradiography using standard procedures (20). At least 10 and at most 20 complete longitudinal sections of full crypts were evaluated per animal for number and position of labeled cells and number of cells along the crypt columns. Labeling indices for whole crypt height, mean position of the uppermost labeled cells and crypt height were determined for each dietary group.

Remaining animals were sacrificed after 8 weeks on their respective diets. Animals were fasted overnight before they were sacrificed. All animals were killed between 9:00 and 11:00 a.m. to minimize potential diurnal variations. The blood serum was obtained from rats and analyzed for their total cholesterol, triglycerides and lipoprotein cholesterol (21). The test methodologies, all run on a Roche Cobas Mira according to the procedure recommended by manufacturer, were as follows. Total cholesterol was assayed using a sequential enzymatic reaction forming a quinoneimmine dye in one step. Triglycerides in serum were hydrolyzed by lipase to free fatty acids and glycerol to form red chromogen. HDL was separated by isoelectric-polyanionic precipitation of LDL, using phosphotungstate as precipitation reagent. HDL cholesterol (HDL-C) was then assayed as described above for total cholesterol. LDL cholesterol (LDL-C) and VLDL cholesterol (VLDL-C) were calculated using the following formulas: VLDL = Triglycerides/5; LDL-C = Total cholesterol−(VLDL-C+HDL-C). These formulas are from human medicine and are not considered valid at triglyceride levels >400 mg/dl). The data obtained is summarized in tables 1–3 below.

TABLE 1

Effect of Dietary Glucarate on Serum Cholesterol Levels in Female Sprague-Dawley Rats[a]

| | AIN-76A | Glucarate-Containing AIN-76A | |
|---|---|---|---|
| | | 17.5 mmol/kg | 35 mmol/kg |
| Total cholesterol | 110.8 ± 2.7 | 100.3 ± 4.0[b] | 95.2 ± 3.7[c] |
| Total Triglycerides | 56.7 ± 4.8 | 54.7 ± 3.5 | 51.4 ± 4.1 |
| HDL-C[d] | 87.3 ± 3.6 | 82.9 ± 3.9 | 79.8 ± 3.4 |
| LDL-C[e] | 9.6 ± 0.9 | 6.7 ± 1.3 | 6.6 ± 0.9[f] |
| VLDL-C[g] | 10.7 ± 0.9 | 10.7 ± 0.7 | 9.3 ± 0.7 |

[a]Each value is the mean (mg/dl) ±S.E., n = 9 per group.
[b]Significantly different from the AIN-76A value: 10% reduction, $p < 0.05$.
[c]Significantly different from the AIN-76A value: 14% reduction, $p < 0.002$.
[d]HDL-C = high density lipoprotein cholesterol.
[e]LDL-C = low density lipoprotein cholesterol.
[f]Significantly different from the AIN-76A value: 30% reduction, $p < 0.05$.
[g]VLDL-C = very low density lipoprotein cholesterol.

As shown in the Table 1 above, dietary glucarate significantly and in a dose dependent fashion reduced serum levels of total cholesterol. The LDL cholesterol reduction by glucarate (35 mmol/kg diet) was also significant. There were no significant differences in triglyceride, HDL-C or VLDL-C levels.

Study of cytokinetics of colonic and small intestine mucosa in the two dietary groups (Table 2) revealed that the rats fed the glucarate containing AIN-76A diet (35 mmol/kg) had significantly lower values for labeling indices and position of the uppermost labeled cells than the corresponding values for the AIN-76A control group. There was no significant difference in colonic crypt height.

TABLE 2

Cytokinetics of Colonic and Small Intestine Mucosa in 55-Day-Old Female Sprague-Dawley Rats Fed AIN-76A and Glucarate-Containing AIN-76A Diets[a]

| | Colon | | Small Intestine | |
|---|---|---|---|---|
| | AIN-76A | AIN-76A + Glucarate[b] | AIN-76A | AIN-76A + Glucarate[b] |
| Crypt column height (cells) | 33.1 ± 0.6 | 32.7 ± 0.6 | 81.4 ± 1.3 | 90.9 ± 1.4 |
| Labeling index (per crypt column) | 4.4 ± 0.5 | 2.8 ± 0.2[c] | 9.4 ± 0.3 | 7.1 ± 0.4[d] |
| Highest labeled cell position | 6.1 ± 0.7 | 5.1 ± 0.6[e] | 19.7 ± 1.5 | 14.8 ± 1.6[e] |

[a]Mean ± S.E.
[b]35 mmol/kg diet.
[c]36% reduction, $p < 0.005$.
[d]25% reduction, $p < 0.0005$.
[e]$p < 0.025$.

EXAMPLE 2

Effect of Dietary Glucarate on Azoxymethane-Induced Colon Tumorigenesis

Six week-old male Sprague-Dawley rats received a single subcutaneous injection of azoxymethane (15mg/kg body weight) (22). Rats were fed normal chow diets containing 140 mmol/kg of either calcium glucarate or calcium gluconate (negative calcium control) beginning 1 week before carcinogen administration. Animals were sacrificed 8 months post-carcinogen treatment and evaluated for the presence of tumors.

TABLE 3

Inhibition of Azoxymethane-Induced Colon Tumorigenesis by Dietary Glucarate

| Treatment | No. of Rats | Rats with Tumors (%) | | | Tumors per Rat | | |
|---|---|---|---|---|---|---|---|
| | | Small Intestine | Colon | Total | Small Intestine | Colon | Total |
| Calcium Gluconate[a] (Control) | 17 | 2 (11.7) | 8 (47.0) | 10 (58.8) | 0.12 ± 0.10 | 0.53 ± 0.05 | 0.65 ± 0.07 |
| Calcium Glucarate[a] | 16 | 0 | 1 (6.2)[b] | 1 (6.2)[b] | 0 | 0.06 ± 0.01[c] | 0.06 ± 0.01[c] |

[a]140 mmol/kg diet.
[b]Significantly different from control group: $p < 0.005$.
[c]Significantly different from control group: $p < 0.05$.

As shown in Table 3, dietary glucarate (140 mmol/kg diet) markedly inhibited azoxymethane-induced tumorigenesis in both the small intestine and colon of the rat. There was no significant difference in tumor incidence or multiplicity between rats fed normal chow and the same chow with the calcium gluconate supplement of 140 mmol/kg. The calcium content itself, increased by 0.56% in the calcium glucarate or gluconate supplemented diets, had no effect on rat colon tumorigenesis. It was previously shown (23) that calcium gluconate inhibits colon carcinogenesis only when high fat diets are fed to rats.

Thus, it is demonstrated that preparations containing glucaric acid significantly reduce serum cholesterol levels without increasing the risk of colon cancer. This appears due to glucarate's surprising antiproliferative effects.

EXAMPLES 3

Vitamin and Mineral Mixtures

The contents of the AIN-76 Mineral Mixture and the AIN-76A Vitamin Mixture are shown in Tables 4 and 5, respectively. These mineral and vitamin mixtures, known from the prior art, were used to prepare the AIN-76A diet used as control diet in Example 1.

TABLE 4

AIN-76 Mineral Mixture[a]

| Ingredient | g/kg mixture |
|---|---|
| Calcium phosphate, dibasic (CaHPO$_4$) | 500.00 |
| Sodium chloride (NaCl) | 74.00 |
| Potassium citrate, monohydrate (K$_3$C$_6$H$_5$O$_7$.H$_2$O) | 220.00 |
| Potassium sulfate (K$_2$SO$_4$) | 52.00 |
| Magnesium oxide (MgO) | 24.00 |
| Manganum carbonate (43–48% Mn) | 3.50 |
| Ferric citrate (16–17% Fe) | 6.00 |
| Zinc carbonate (70% ZnO) | 1.60 |
| Cupric carbonate (53–55% Cu) | 0.30 |
| Potassium iodate (KIO$_3$) | 0.01 |
| Sodium selenite (Na$_2$SeO$_3$.5H$_2$O) | 0.01 |

TABLE 4-continued

AIN-76 Mineral Mixture[a]

| Ingredient | g/kg mixture |
|---|---|
| Chromium potassium sulfate (CrKSO$_4$.12H$_2$O) | 0.55 |
| Sucrose, finely powdered | 118.00 |

[a]To be used at 3.5% of the diet (Journal of Nutrition 107:1340–1348, 1977).

TABLE 5

AIN-76 Vitamin Mixture[a]

| Vitamin | g/kg mixture |
|---|---|
| Thiamine.HCl | 0.60 |
| Riboflavin | 0.60 |
| Pyridoxine.HCl | 0.70 |
| Niacin | 3.00 |
| Calcium Pantothenate | 1.60 |
| Folic acid | 0.20 |
| D-Biotin | 0.02 |
| Vitamin B$_{12}$ (0.1%) | 1.00 |
| Retinyl palmitate (500,000 U/g) | 0.80 |
| dl-α-Tocopherol acetate (500 U/g) | 10.00 |
| Cholecalciferol (400,000 U/g) | 0.25 |
| Menadione sodium bisulfite | 0.08 |
| Sucrose, finely powdered | 981.15 |

[a]To be used at 1% of diet (Journal of Nutrition 107:1340–1348, 1977; 110:1726, 1980).

EXAMPLE 4

Mineral Formulas With Glucarate

The contents of four mineral formulas containing glucarate are shown in Table 6. These formulas were used to prepare the modified AIN-76A diets used as experimental diets in Example 1 (formulas 1 and 2) and Example 6 (formulas 3 and 4).

TABLE 6

Glucarate-Containing Mineral Formulas[a]

| | g/kg mixture | | | |
|---|---|---|---|---|
| Ingredient | Formula 1 | Formula 2 | Formula 3 | Formula 4 |
| Calcium phosphate, dibasic (CaHPO$_4$) | 366.00 | 433.00 | 500.00 | 500.00 |
| Calcium D-glucarate (CaC$_6$H$_8$O$_8$3.5H$_2$O) | 300.00 | 150.00[c] | — | — |
| Sodium chloride (NaCl) | 74.00 | 74.00 | 74.00 | 74.00 |
| Potassium citrate, monohydrate (K$_3$C$_6$H$_5$O$_7$.H$_2$O) | — | 110.00 | 100.00 | 168.00 |
| Potassium phosphate dibasic (K$_2$HPO$_4$) | 172.00 | 86.00 | — | — |
| Potasium hydrogen Dglucarate (KC$_6$H$_7$O$_8$) | — | — | 238.00[b] | 119.00[c] |
| Potassium sulfate (K$_2$SO$_4$) | 52.00 | 52.00 | 52.00 | 52.00 |
| Magnesium oxide (MgO) | 24.00 | 24.00 | 24.00 | 24.00 |
| Magnesium carbonate (43–48% Mn) | 3.50 | 3.50 | 3.50 | 3.50 |
| Ferric citrate (16–17% Fe) | 6.00 | 6.00 | 6.00 | 6.00 |
| Zinc carbonate (70% ZnO) | 1.60 | 1.60 | 1.60 | 1.60 |
| Cupric carbonate (53–55% Cu) | 0.30 | 0.30 | 0.30 | 0.30 |
| Potassium iodate (KIO$_c$) | 0.01 | 0.01 | 0.01 | 0.01 |
| Sodium selenite (Na$_2$SeO$_3$.5H$_2$O) | 0.01 | 0.01 | 0.01 | 0.01 |
| Chromium potassium sulfate (CrKSO$_4$.12H$_2$O) | 0.55 | 0.55 | 0.55 | 0.55 |
| Sucrose, finely powdered | — | 59.00 | — | 51.00 |

[a]To be used at 3.5% of the diet.
[b]34 mmoles of glucarate per kg diet.
[c]17 mmoles of glucarate per kg diet.

EXAMPLE 5

Antiproliferative Effect of Nutritional Formulas Containing glucarate

Two modified AIN-76A diet at the concentration of 17 or 34 mmol/kg diet as described in Examples 1 and 4. Specifically, 35 g of the glucarate-containing mineral Formula 1 or 2 (see Table 6) and 10 g of the AIN-76A vitamin mixture (see Table 5) were used per 1 kg AIN-76A diet. Two other experimental diets were prepared by simply supplementing the AIN-76A diet with 70 mmol/kg diet of calcium D-glucarate or calcium 1-tartrate (negative calcium control). Female virgin Sprague-Dawley rats were fed the AIN-76A diet, the same diet plus calcium D-glucarate or calcium L-tartrate, or the modified AIN-76A diets beginning at 40 days of age. After 4 weeks on their respective diets the rats were sacrificed and DNA labeling indices were measured as described in Example 1.

As shown in Table 7, when calcium D-glucarate was incorporated into a mineral composition at the concentration of 34 mmol/kg diet, the DNA synthesis-reducing effect of this formula on the mammary gland epithelium was 3.5–4 times greater than that of the 2-fold higher concentration (70 mmol/kg diet) of calcium D-glucarate used simply as the additive. This result is unexpected and proves the benefit of use of glucarate as a component of mineral and vitamin formulas. Calcium alone had some effect on the mammary gland and colon epithelia but not on the urinary bladder epithelium.

TABLE 7

Effect of Dietary Glucarate on DNA Labeling Index in Female Virgin Sprague-Dawley Rats

| | Content | | Labeling Index (% or per colon crypt)[a] | | | |
|---|---|---|---|---|---|---|
| | (mmol/kg diet) | | Mammary Gland | | | Urinary |
| Diet | Glucarate | Calcium | Buds | Ducts | Colon | Bladder |
| AIN-76A | None | 130 | 19.97 ± 1.25[a] | 13.42 ± 1.19 | 11.12 ± 0.89 | 0.51 ± 0.12[a] |
| AIN-76A + Ca Tartrate | None | 200 | 15.27 ± 0.66 | 7.60 ± 0.57 | 8.21 ± 1.01 | 0.36 ± 0.08[a] |
| AIN-76A + Ca Glucarate | 70 | 200 | 2.85 ± 0.90 | 0.57 ± 0.15 | 4.58 ± 0.36[a] | 0.32 ± 0.04[a] |
| Modified AIN-76A with glucarate | 34 | 130 | 0.81 ± 0.15 | 0.24 ± 0.10 | 4.19 ± 0.54[a] | 0.08 ± 0.04 |

[a]Mean ± Student's t-tests were performed in all possible diet comparisons. For all comparisons but those marked with asterisks, the difference were significant (the p-values ranged from 0.0005 to 0.025).

EXAMPLE 6

Hypocholesterolemic effect of Glucarate-Containing Nutritional Formulas

A normal fat diet (pelleted corn starch AIN-76A diet) and a high fat diet containing 5% and 20% fat, respectively, were prepared as described in the prior art (Dyets, Inc. 1981/1988 catalog: Experimental Diets & Ingredients for Laboratory Animals). Two high fat diets were prepared by incorporating potassium hydrogen D-glucarate at the concentration of 17 or 34 mmol/kg diet using the mineral formulas 3 and 4 as described in Example 4 (see Table 6). Female virgin Sprague-Dawley rats were fed these experimental diets or control diets for 4 weeks beginning at 44 days of age. The rats were sacrificed and the blood was assayed for total cholesterol, total triglycerides, HDL-C, LDL-C and VLDL-C as described in Example 1. The results are shown in Table 8.

The hypercholesterolemic high fat diet increased the serum levels of total cholesterol and LDL cholesterol 1.2-fold and 2.3-fold, respectively. However, the increased total cholesterol and LDL cholesterol levels were reduced by 12% (p<0.05) and 35% (0.02) respectively by using the glucarate mineral Formula 3 of Example 4 (34 mmol glucarate per kg high fat diet).

TABLE 8

Effect of Dietary Glucarate on Serum Cholesterol Levels[a] in Female Sprague-Dawley Rats Fed Hypercholesterolemic Diets

| Diet | Glucarate (mmol/kg diet) | Fat (%) | Total Cholesterol | Total TriGlycerides | HDL-C[b] | LDL-C[c] | VLDL-C[d] |
|---|---|---|---|---|---|---|---|
| NFD[e] | None | 5 | 87.0 ± 5.6 | 26.8 ± 4.8 | 71.8 ± 7.7 | 10.0 ± 2.2 | 5.1 ± 1.1 |
| HFD[f] | None | 20 | 105.6 ± 4.5 | 31.0 ± 2.4 | 76.1 ± 3.8 | 23.3 ± 1.4 | 6.1 ± 0.4 |
| HFD with Glucarate | 34 | 20 | 92.4 ± 4.1[g] | 25.7 ± 1.7 | 72.3 ± 3.3 | 15.1 ± 1.4[h] | 5.0 ± 0.3 |
| HFD with glucarate | 17 | 20 | 101.3 ± 5.4 | 32.1 ± 3.7 | 73.4 ± 3.1 | 21.6 ± 2.1 | 6.3 ± 0.8 |

[a]Each value is the mean (mg/dl) ±S.E.; n = 7.
[b]HDL-C = high density lipoprotein cholesterol.
[c]LDL-C = low density lipoprotein cholesterol.
[d]VLDL-C = Very low density lipoprotein cholesterol.
[e]NFD = normal fat diet (corn starch AIN-76A diet; J. Nutr. 107:1341, 1977; 110:1726, 1980) containing 5% corn oil.
[f]HDF = high fat diet containing 20% corn oil.
[g]Significantly different from the high fat diet value: 12% reduction (p < 0.05).
[h]Significantly different from the high fat diet value: 35% reduction (p < 0.02).

EXAMPLE 7

Pharmaceutical Formulas Containing Glucarate

The chemical contents and vitamin and mineral contents of two pharmaceutical formulas containing glucarate are shown in Table 9 and 10, respectively. Both formulas contain magnesium and potassium and vitamin D. The calcium to phosphorus ratios remain within the physiologically required range of 1.3 to 1 or 1 to 1. Calcium D-glucarate is used as a source of glucarate.

TABLE 9

Chemical Content of Two Pharmaceutical Formulas with Glucarate[a]

| | Amount[b] | |
|---|---|---|
| Active Ingredient | Formula 1[c] | Formula 2[d] |
| Cholecalciferol | 1.25 μg | 1.25 μg |
| Calcium Phosphate, dibasic (CaHPO$_4$) | 374.15 mg | 374.15 mg |
| Calcium D-glucarate (CaC$_6$H$_8$O$_8$4H$_2$O) | 320.20 mg | 320.20 mg |
| Potassium phosphate, dibasic (K$_2$HPO$_4$) | 363.50 mg | 169.00 mg |
| Magnesium oxide (MgO) | 83.90 mg | 82.90 mg |

[a]For vitamin and mineral content see Table 10.
[b]Per tablet, capsule, caplet or wafer.
[c]Calcium to phosphorus ratio 1 to 1.
[d]Calcium to phosphorus ratio 1.3 to 1.

TABLE 10

Vitamin and Mineral Content of Two Pharmaceutical Formulas with Glucarate[a]

| | Formula 1[b] | | Formula 2[c] | |
|---|---|---|---|---|
| Vitamin or Mineral | Amount[d] | % U.S. RDA[e] | Amount[d] | % U.S. RDA[e] |
| Vitamin D | 50 IU | 12.5 | 50 IU | 12.5 |
| Calcium | 150 mg | 12.5 | 150 mg | 12.5 |
| Phosphorus | 150 mg | 12.5 | 115 mg | 9.6 |
| Magnesium | 50 IU | 12.5 | 50 mg | 12.5 |
| Potassium | 163 mg | N.D.[f] | 76 mg | N.D.[f] |
| Glucarate | 209 mg | N.D.[f] | 209 mg | N.D.[f] |

[a]For chemical content see Table 9.
[b]Calcium to phosphorus ratio 1 to 1.
[c]Calcium to phosphorus ratio 1.3 to 1.
[d]Per tablet, capsule, caplet or wafer. The highest recommended dose (Recommended Dietary Allowances, 10th Edition, NAP, Washington, D.C. 1989).
[e]U.S. Recommended Daily Allowance has not been established.
[f]N.D. = Not Determined.

EXAMPLE 8

A Vitamin and Mineral Supplement with Glucarate

Table 11 shows the vitamin and mineral content of a pharmaceutical formula with glucarate provided in the form of potassium hydrogen D-glucarate.

TABLE 11

A Vitamin and Mineral Pharmaceutical Formula with Glucarate

| Vitamin or Mineral | Amount[a] | % U.S. RDA[b] |
|---|---|---|
| Vitamin D[c] | 50 IU | 12.5 |
| Calcium[d] | 150 mg | 12.5 |
| Phosphorus[e] | 115 mg | 12.5 |
| Magnesium[f] | 50 mg | 12.5 |
| Potassium[g] | 39 mg | N.D.[h] |
| Glucarate[g] | 209 mg | N.D.[h] |

[a]Per tablet, capsule, caplet or wafer.
[b]The highest dose recommended (Recommended Dietary Allowances, 10th Edition, NAP, Washington, D.C., 1989).
[c]As cholecalciferol (1.25 μg).
[d]As calcium phosphate, dibasic (510.2 mg).
[e]As calcium phosphate, dibasic (see above). Calcium to phosphate ratio 1.3 to 1.
[f]As magnesium oxide (82.90 mg).
[g]As potassium hydrogen D-glucarate (248.2 mg).
[h]N.D. = Not Determined.

EXAMPLE 9

Multi-Vitamin and Multi-Mineral Formula Containing Glucarate

The contents of multi-vitamin and mineral formula with glucarate designed to provide recommended dietary allowances of vitamins, minerals and trace elements, is shown in Table 12. Eight tablets, capsules, caplets or wafers, two of them to be taken at breakfast, lunch, dinner, and supper, provide RDA.

TABLE 12

A Multi-Vitamin and Multi-Mineral Formula with Glucarate

| Vitamin, Mineral or Trace Element | Amount[a] | % U.S. RDA[b] |
|---|---|---|
| Vitamin A[c] | 162.5 RE | 12.5 |
| Vitamin D[d] | 50.0 IU | 12.5 |
| Vitamin E[e] | 1.5 α-TE | 12.5 |
| Vitamin K | 10.0 μg | 12.5 |
| Vitamin C | 12.0 mg | 12.5 |
| Thiamin | 0.2 mg | 12.5 |
| Riboflavin | 225.0 μg | 12.5 |
| Niacin[f] | 2.5 NE | 12.5 |
| Vitamin $B_6$ | 275.0 μg | 12.5 |
| Folate | 50.0 μg | 12.5 |
| Vitamin $B_{12}$ | 325.0 ng | 12.5 |
| Biotin | 12.5 μg | 12.5[g] |
| Panthothenic acid | 875.0 μg | 12.5 |
| Calcium[h] | 150.0 mg | 12.5 |
| Phosphorus[i] | 150.0 mg | 12.5 |
| Magnesium | 50.0 mg | 12.5 |
| Iron | 3,750.0 μg | 12.5 |
| Zinc | 1,875.0 μg | 12.5 |
| Iodine | 25.0 μg | 12.5 |
| Selenium | 9.5 μg | 12.5 |
| Copper | 375.0 μg | 12.5[g] |
| Manganese | 625.0 μg | 12.5[g] |
| Fluoride | 500.0 μg | 12.5[g] |
| Chromium | 25.0 μg | 12.5[g] |
| Molybdenum | 32.0 μg | 12.5[g] |
| Potassium[j] | 163.0 mg | N.D.[k] |
| Glucarate[l] | 209.0 mg | |

[a]Per tablet, capsule, caplet or wafer.
[b]The highest dose recommended (Recommended Dietary Allowances, 10th Edition, NAP, Washington, D.C., 1989).
[c]1 Retinol Equivalent (RE) = 1 μg retinol or 6 μg β-carotene or an equivalent amount of a retinoic acid compound.
[d]As cholecalciferol. 10 μg cholecalciferol = 400 IU of vitamin D.
[e]α-Tocopherol Equivalent (α-TE) = 1 mg d-α-tocopherol.
[f]1 Niacin Equivalent (NE) = 1 mg of niacin.
[g]The highest estimated safe or adquate dose (ibid.).
[h]As calcium phosphate, dibasic (374.15 mg) and calcium D-glucarate tetrahydrate (320.2 mg).
[i]As calcium phosphate, dibasic (see above) and potassium phosphate, dibasic (363.50 mg). Calcium to Phosphorus ratio 1 to 1.
[j]As potassium phosphate, dibasic (see above).
[k]N.D. = Not Determined.
[l]As calcium D-glucarate (see above).

EXAMPLE 10

High-Potency Multi-Vitamin and Multi-Mineral Formula Containing Glucarate

The contents of high-potency multivitamin and mineral disease-preventative formula with glucarate is shown in Table 13. Four tablets or packets, each to be taken at breakfast, lunch, dinner and supper, provide shown % RDA of vitamins and minerals.

TABLE 13

A High Potency Multi-Vitamin and Mineral Formula with Glucarate

| Vitamin or Mineral | Amount[a] | % U.S. RDA[b] |
|---|---|---|
| Vitamin A[c] | 1,300.0 RE | 100 |
| Vitamin D[d] | 400.0 IU | 100 |
| Vitamin E[e] | 48.0 α-TE | 400 |
| Vitamin C | 768.0 mg | 800 |
| Thiamin | 40.0 mg | 2500 |
| Riboflavin | 4,140.0 μg | 230 |
| Niacin[f] | 40.0 NE | 200 |
| Vitamin $B_6$ | 44.0 mg | 2000 |
| Folate | 400.0 μg | 100 |
| Vitamin $B_{12}$ | 41.6 μg | 1600 |
| Pantothenic acid | 56.0 mg | 800[g] |
| Calcium[h] | 600.0 mg | 50 |
| Phosphorus[i] | 600.0 mg | 50 |
| Magnesium | 200.0 mg | 50 |
| Zinc | 15.0 mg | 100 |
| Selenium | 76.0 μg | 100 |
| Potassium[j] | 652.0 mg | N.D.[k] |
| Glucarate | 832.0 mg | N.D.[k] |

[a]Per four tablets or packets.
[b]The highest dose recommended (Recommended Dietary Allowances, 10th Edition, NAP, Washington, D.C., 1989).
[c]1 Retinol Equivalent (RE) = 1 μg retinol or 6μ β-carotene, or an equivalent amount of a retinoic acid compound.
[d]As cholecalciferol. 10 μg cholecalciferol = 400 IU of Vitamin D.
[e]α-Tocopherol Equivalent (α-TE) = 1 mg d-α-tocopherol.
[f]1 Niacin Equivalent (NE) = 1 mg of niacin.
[g]The highest estimated safe or adequate dose (ibid.).
[h]As calcium phosphate, dibasic (1,496.6 mg) and calcium D-glucarate, tetrahydrate, (1,280.0 mg).
[i]As calcium phosphate, dibasic (see above) and potassium phosphate, dibasic (1,454.0 mg). Calcium to phosphorus ratio 1 to 1.
[j]As potassium phosphate, dibasic (see above).
[k]N.D. = Not Determined.
[l]As calcium D-glucarate (see above).

EXAMPLE 11

Glucarate-Containing Chemically Defined Diet for Enteral Nutrition

The contents of a chemically defined diet with glucarate is shown in Table 14. This is an example of a nutritionally complete, elemental diet for enteral nutrition. Table 15 describes acceptable ranges of these components.

TABLE 14

A Chemically Defined Diet with Glucarate

| Ingredient | Amount[a] | % U.S. RDA[b] |
|---|---|---|
| Macroconstituents: | | |
| Amino Acids (Free) | 37.1 g | |
| Carbohydrates (Predigested) | 407.4 g | |
| Fat | 2.6 g | |
| Linoleic acid | 2.1 g | |
| Vitamins, Minerals, Electrolytes, Trace Elements: | | |
| Vitamin A[c] | 1300.0 RE | 100 |
| Vitamin D[d] | 400.0 IU | 100 |
| Vitamin E[e] | 12.0 α-TE | 100 |
| Vitamin K | 80.0 mg | 100 |
| Vitamin C | 96.0 mg | 100 |
| Thiamin | 1.6 mg | 100 |
| Riboflavin | 1.8 mg | 100 |
| Niacin[f] | 20.0 NE | 100 |
| Vitamin $B_6$ | 2.2 mg | 100 |
| Folate | 400.0 μg | 100 |
| Vitamin $B_{12}$ | 2.6 mg | 100 |
| Biotin | 100.0 μg | 100[g] |
| Pantothenic acid | 7.0 mg | 100[g] |
| Calcium[h] | 1,200.0 mg | 100 |
| Phosphorus[i] | 1,200.0 mg | 100 |
| Magnesium | 400.0 mg | 100 |
| Iron | 30.0 mg | 100 |
| Zinc | 15.0 mg | 100 |
| Iodine | 200.0 μg | 100 |
| Selenium | 75.0 μg | 100 |
| Copper | 3.0 mg | 100[g] |
| Manganese | 5.0 mg | 100[g] |
| Fluoride | 1.0 μg | 100[g] |
| Chromium | 200.0 μg | 100[g] |
| Molybdenum | 250.0 μg | 100[g] |
| Choline | 73.3 mg | N.D.[j] |
| Sodium | 842.4 mg | N.D. |
| Potassium[k] | 2,110.0 mg | N.D. |
| Chloride | 1,710.0 mg | N.D. |
| Acetate | 995.0 mg | N.D. |
| Glucarate[l] | 3,525.0 mg | N.D. |

[a]Per six packets. One packet to be diluted with water to a total standard dilution volume of 300 ml.
[b]The highest dose recommended (Recommended Dietary Allowances, 10th Edition, NAP, Washington, D.C., 1989).
[c]1 Retinol Equivalent (RE) = 1 μg retinol or 6 μg β-carotene or an equivalent amount of a retinoic acid compound.
[d]As cholecalciferol. 10 μg cholecalciferol = 400 IU of vitamin D.
[e]α-Tocopherol Equivalent (α-TE) = 1 mg d-α-tocopherol.
[f]1 Niacin Equivalent (NE) = 1 mg of niacin.
[g]The highest estimated safe or adquate dose (ibid.).
[h]As calcium phosphates.
[i]As calcium and potassium phosphates.
[j]N.D. = Not Determined.
[k]As potassium phosphate and potassium hydrogen D-glucarate.
[l]As potassium hydrogen D-glucarate.

TABLE 15

A Chemically Defined Diet with Glucarate

7–15% by weight of Amino Acids

76–86% by weight of Carbohydrates 0.4–1.2% by weight of Fat 0.4–1.0% by weight of Linoleic acid, and 1,200.0–1,800.0 RE of Vitamin A 400.0–600.0 IU of Vitamin D 12.0–18.0 α-TE of Vitamin E 80.0–120.0 mg of Vitamin K 96.0–480.0 mg of Vitamin C 1.6–3.2 mg of Thiamin 1.8–3.6 mg of Riboflavin 20.0–40.0 NE of Niacin 2.2–4.4 mg of Vitamin $B_6$ 400.0–800.0 μg of Folate 2.6–5.2 mg of Vitamin $B_{12}$ 100.0–200.0 μg of Biotin 7.0–14.0 mg of Pantothenic acid 1,000.0–1,200.0 mg of Calcium 1,000.0–1,200.0 mg of Phosphorus 350.0–400.0 mg of Magnesium 15.0–30.0 mg of Iron 15.0–22.5 mg of Zinc 150.0–200.0 μg of Iodine 50.0–150.0 μg of Selenium 2.0–3.0 mg of Copper 2.0–5.0 mg of Manganese 0–4.0 mg of Fluoride 0–200.0 μg of Chromium 0–250.0 μg of Molybdenum 72.0–720.0 mg of Choline 840.0–845.0 mg of Sodium 2,110.0–2,400.0 mg of Potassium 1,620.0–1,710.0 mg of Chloride, 0–1,000.0 mg of Acetate, and 1,750.0–7,050.0 mg of Glucarate.

While the invention is susceptible to various modifications and alternative forms, a specific embodiment thereof has been shown by way of example and was described above in detail. It should be understood, however, that it is not intended to limit the invention to the particular forms disclosed, but on the contrary, the intention is to cover all modifications, equivalents, and alternatives falling within the spirit and scope of the invention as defined by the appended claims.

The following citations are incorporated in pertinent part by reference herein for the reasons cited above.

1. Sutherlands, N. H. F., Temple, W. A., Nye, E. R. and Herbison, G. P., 1980, Am. J. Clin. Nutr. 33:2581.
2. Barret-Connor, E., Witzmum, J. L. and Holdbrook, M., 1983, Am. J. Epidemiology 117:186.
3. Nigro, N. D., Campbell, R. L., Gantt, J. S. et al., 1977, Cancer Res. 37:3198.
4. Nigro, N. D., Bhadrachri, N. and Chomachai, C., 1973, Dis. Colon Rectum 16: 438.
5. Marsh, C. A., 1963, Biochem, J. 87:82.
6. Masaki, H., 1972, Nippon Hifuka Gakkai Zashi, 82:151, 233; Chem. Abstr., 78: 2709b, 27062u.
7. Levvy, G. A. and Conchie, J., 1966, in Dutton, G. J. (ed.), Glucuronic Acid,: Academic Press, New York, p. 301.
8. Mocarelli, P., Brambilla, P., Colombo, L., Marocchi, A., Crespi, C., Tramacere, P., Mondonica, A., 1989, Clin. Chem. 34:2283.
9. Yokoyama, M., Matsuoka, S. and Wakui, A. Recent Adv. Chemother, Proc. Int. conqr. Chemother, 14th, 1985, Univ. Tokyo Press, Tokyo, Japan.
10. Kringstad, R. and nordal, A., 1975, Phytochemistry, 14: 1868.
11. Elliger, C. A., Lundin, R. E. and Haddon, W. F., 1981, Phytochemistry, 20:1133.
12. Walaszek, Z., Hanausek-Walaszek, M. and Webb, T. E., 1984, Proc. Am. Assoc. Cancer Res., 25:128.
13. Kessler, G., Neufeld, E. F., Feingold, G. S. and Hassid, W., 1961, J. Biol Chem., 236:308.
14. Ambrose, A.M., 1951, J. Am. Pharm, Assoc. 40:277.
15. Carr, C. J., 1947, Proc. Soc. Exptl, Biol. Med. 65:189.
16. Walaszek, Z., Hanausek-Walaszek, M., Minton, J. P. and Webb, T. E., 1986, Carcinogenesis, 7:1463.
17. Walaszek, Z., Hanausek-Walaszek, M., Webb, T. E., 1986, Cancer Lett., 33:25.
18. Ad Hoc Committee on Standards for Nutritional Studies, 1977, J. Nutr., 107:1340.
19. Ad Hoc Committee on Standards for Nutritional Studies, 1980, J. Nutr., 110:1726.
20. Bird, R. P., Schneider, R., Stamp, D. and Bruce, W. R., 1986, Carcinogenesis 7:1657.
21. Lindgren, F. T., 1975, in Perkins, E.G. (ed.) Analysis of Lipids and Lipoproteins, Am. Oil Chemists' Society, Champagne, Il., p. 204.
22. Ward, J. M., 1975, Vet. Pathol. 12:165.
23. Pence, B. C. and Buddingh, F., 1988, Carcinogenesis 9:187.

What is claimed is:

1. A method for the prevention or treatment of non-cancerous cellular hyperproliferation, the method comprising administering to an animal in need thereof a pharmaceutical formulation including a prophylactically therapeutically effective amount of glucaric acid or a pharmaceutically acceptable salt thereof.
2. The method of claim 1 wherein said animal is a human.
3. The method of claim 1 wherein said pharmaceutical formulation is a tablet, capsule, suspension, or solution.
4. The method of claim 1 wherein the administration is enteral.
5. The method of claim 1 wherein the administration is intravenous, intraarterial, subcutaneous, intramuscular, intralymphatic, intraperitoneal, or intrapleural.
6. The method of claim 1 or 4 wherein said formulation is a sustained release formulation.
7. The method of claim 6 wherein said administration is once daily.
8. The method of claim 1 wherein said therapeutically effective amount is from about 10 mg to about 16,000 mg, daily.
9. The method of claim 1 wherein said therapeutically effective amount is from about 200 mg to about 8,000 mg, daily.
10. The method of claim 1 wherein said pharmaceutically acceptable salt is one salt selected from the group consisting of calcium glucarate, sodium glucarate, potassium hydrogen glucarate, and magnesium glucarate.
11. The method of claim 1 wherein said pharmaceutically acceptable salt is selected from the group consisting of potassium hydrogen glucarate and calcium glucarate.
12. A method for the prevention or treatment of non-cancerous cellular hyperproliferation comprising administering daily to a human in need thereof a sustained release pharmaceutical formulation including from about 10 mg to about 2,000 mg of glucaric acid or a pharmaceutical acceptable salt thereof.
13. The method of claim 12 wherein said sustained release pharmaceutical formulation further includes a multiplicity of vitamins, minerals and micronutrients.
14. A method for the prevention of non-cancerous cellular hyperproliferation in a population of humans or animals, the method comprising the steps of:
    (a) adding to a selected foodstuff a predetermined amount of glucaric acid or a pharmaceutical acceptable salt thereof; and
    (b) providing a sufficient quantity of said foodstuff to humans or other animals in need thereof such that said humans or animals may ingest a therapeutically effective amount of glucaric acid or a pharmaceutically acceptable salt thereof.
15. A method for preventing or treating noncancerous cellular hyperproliferation and reducing total serum cholesterol and low density lipoprotein cholesterol in a human or animal subject, the method including the step of administering daily to an individual from one to eight oral sustained release tablets or capsules, each including from about 0.01 to about 100.0% by weight of glucaric acid or a pharmaceutically acceptable salt thereof.
16. The method of claim 15 wherein said tablets or capsules consist essentially of:

Vitamin A
Vitamin D
Vitamin E
Vitamin K
Vitammn C
Thiamin
Riboflavin
Niacin
Vitamin B6
Folate
Vitamin B12
Biotin
Pantothenic acid Calcium
Phosphorus
Magnesium
Iron
Zinc
Iodine
Selenium
Copper
Manganese
Fluoride
Chromium
Molybdenum
Potassium and
Glucaric acid or Glucarate.

17. The method of claim 15 wherein said tablets or capsules consist essentially of:
1.0–130,000 RE of Vitamin A
1.0–40,000 IU of Vitamin D
1.0–1,200 α-TE of Vitamin E
1.0–1,600.0 mg of Vitamin K
1.0–1,800.0 mg of Vitamin C
1.0–160.0 mg of Thiamin
1.0–180.0 µg of Riboflavin
1.0–2,000.0 NE of Niacin
1.0–220.0 mg of Vitamin B6
1.0–40.0 mg of Folate
1.0–260.0 µg of Vitamin B12
1.0–10.0 mg of Biotin
1.0–700.0 mg of Pantothenic acid
1.0–1,800.0 mg of Calcium
1.0–1,800.0 mg of Phosphorus
1.0–1,500.0 mg of Magnesium
1.0–1,000.0 mg of Iron
1.0–1,500.0 mg of Zinc
1.0–20.0 mg of Iodine
1.0–7,600.0 µg of Selenium
1.0–300.0 mg of Copper
1.0–500.0 mg of Manganese
1.0–400.0 mg of Fluoride
1.0–20.0 mg of Chromium
1.0–25.6 mg of Molybdenum
1.0–1,800.0 mg of Potassium, and
200–8,000.0 mg of Glucaric acid or Glucarate.

18. The method of claim 15 wherein said tablets or capsules consist essentially of:
Vitamin D
Calcium
Phosphorus
Magnesium
Potassium, and
Glucaric acid or Glucarate.

19. The method of claim 18 where glucarate is potassium hydrogen D-glucarate.

20. The method of claim 18 wherein the following constituents are present in said tablets or capsules within the indicated range of weights or measures:
1.0–40,000 IU of Vitamin D
1.0–1,800.0 mg of Calcium
1.0–1,800.0 mg of Phosphorus
1.0–1,500.0 mg of Magnesium
1.0–1,800.0 mg of Potassium, and
200–8,000 mg of Glucaric Acid or Glucarate.

21. The method of claim 15 wherein said tablets or capsules consist essentially of:
from 200–8,000 mg of glucaric acid or a pharmaceutically acceptable salt thereof.

22. A method for preventing or treating noncancerous cellular hyperproliferation and reducing total serum cholesterol and low density lipoprotein cholesterol in a human or animal subject, the method including the step of administering daily to an individual from one to eight oral sustained release tablets or capsules, each including from about 200 to about 8,000 mg of glucaric acid or a pharmaceutically acceptable salt thereof.

23. A method for the prevention or treatment of noncancerous cellular hyperproliferation and reducing total serum cholesterol and low density lipoprotein cholesterol in a human or animal subject, the method including the step of providing daily to an individual a quantity of a foodstuff including from about to about 8,000 mg of glucaric acid or a pharmaceutically acceptable salt thereof.

24. The method of claim 23 wherein said foodstuff includes a supplement comprising the following constituents:
Amino Acids
Carbohydrates
Fat
Linoleic acid
Vitamin A
Vitamin D
Vitamin E
Vitamin K
Vitamin C
Thiamin
Riboflavin
8 Niacin
Vitamin B6
Folate
Vitamin B12
Biotin
Pantothenic acid
Calcium compound
Phosphorus compound
Magnesium
Iron
Zinc
Iodine
Selenium
Copper
Manganese
Fluoride
Chromium
Molybdenum
Potassium
Chloride, and
Glucaric acid or Glucarate.

* * * * *